(12) United States Patent
Xu et al.

(10) Patent No.: US 7,960,099 B2
(45) Date of Patent: *Jun. 14, 2011

(54) WHITE BLOOD CELL DIFFERENTIATION REAGENT CONTAINING AN ASYMMETRIC CYANINE FLUORESCENT DYE AND METHOD OF USE THEREOF

(75) Inventors: Bing Xu, Shenzhen (CN); Baohua Zhang, Shenzhen (CN); Yuji Kuang, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 731 days.

This patent is subject to a terminal disclaimer.

(21) Appl. No.: 11/967,897

(22) Filed: Dec. 31, 2007

(65) Prior Publication Data

US 2009/0023129 A1    Jan. 22, 2009

(30) Foreign Application Priority Data

Jul. 20, 2007    (CN) .......................... 2007 1 0139172

(51) Int. Cl.
 *A01N 1/02* (2006.01)
 *G01N 33/48* (2006.01)
 *C07D 215/00* (2006.01)
(52) U.S. Cl. ............... 435/2; 436/63; 436/800; 546/165
(58) Field of Classification Search .................. None
See application file for complete search history.

(56) References Cited

U.S. PATENT DOCUMENTS

| | | |
|---|---|---|
| 3,883,274 A | 5/1975 | Vuaille |
| 4,122,348 A | 10/1978 | Bruck |
| 4,146,604 A | 3/1979 | Kleinerman |
| 4,286,963 A | 9/1981 | Ledis et al. |
| 4,325,706 A | 4/1982 | Gershman et al. |
| 4,332,785 A | 6/1982 | Allen et al. |
| 4,336,029 A | 6/1982 | Natale |
| 4,414,325 A | 11/1983 | Masuda et al. |
| 4,447,547 A | 5/1984 | Allen et al. |
| 4,485,175 A | 11/1984 | Ledis et al. |
| 4,528,274 A | 7/1985 | Carter et al. |
| 4,529,705 A | 7/1985 | Larsen |
| 4,544,546 A | 10/1985 | Wang et al. |
| 4,571,388 A | 2/1986 | O'Connell et al. |
| 4,596,035 A | 6/1986 | Gershman et al. |
| 4,617,275 A | 10/1986 | Matsuda et al. |
| 4,637,986 A | 1/1987 | Brown et al. |
| 4,707,451 A | 11/1987 | Sage et al. |
| 4,745,071 A | 5/1988 | Lapicola et al. |
| 4,822,745 A | 4/1989 | Burns et al. |
| 4,882,284 A | 11/1989 | Kirchanski et al. |
| 4,883,867 A | 11/1989 | Lee et al. |
| 4,933,293 A | 6/1990 | Kuroda et al. |
| 4,957,870 A | 9/1990 | Lee et al. |
| 4,971,917 A | 11/1990 | Kuroda |
| 4,978,624 A | 12/1990 | Cremins et al. |
| 4,981,803 A | 1/1991 | Kuroda |
| 4,985,174 A | 1/1991 | Kuroda et al. |
| 5,039,613 A | 8/1991 | Matsuda et al. |
| 5,075,556 A | 12/1991 | Fan et al. |
| 5,116,539 A | 5/1992 | Hamaguchi et al. |
| 5,155,044 A | 10/1992 | Ledis et al. |
| 5,175,109 A | 12/1992 | Sakata et al. |
| 5,179,026 A | 1/1993 | Matsuda et al. |
| 5,180,677 A | 1/1993 | Di Ianni et al. |
| 5,188,935 A | 2/1993 | Leif et al. |
| 5,227,304 A | 7/1993 | Wong |
| 5,232,857 A | 8/1993 | Lefevre et al. |
| 5,242,832 A | 9/1993 | Sakata |
| 5,250,437 A | 10/1993 | Toda et al. |
| 5,264,369 A | 11/1993 | Sakata et al. |
| 5,284,771 A | 2/1994 | Fan et al. |
| 5,316,725 A | 5/1994 | Carver et al. |
| 5,316,951 A | 5/1994 | Carver et al. |
| 5,321,130 A | 6/1994 | Yue et al. |
| 5,350,695 A | 9/1994 | Colella et al. |
| 5,360,739 A | 11/1994 | Fan et al. |

(Continued)

FOREIGN PATENT DOCUMENTS

CN    1101980    4/1995

(Continued)

OTHER PUBLICATIONS

Notice of Allowance dated Feb. 22, 2010 for U.S. Appl. No. 12/482,335.

(Continued)

*Primary Examiner* — Sandra Saucier (74) *Attorney, Agent, or Firm* — Stoel Rives, LLP (57) ABSTRACT

The present disclosure provides a white blood cell differentiation reagent comprising a fluorescent dye compound of Formula I, wherein $R_1$, $R_2$, $R_3$, $R_4$, $Y^-$ and n are as defined in the specification. The present disclosure also provides a white blood cell detection kit comprising the white blood cell differentiation reagent, and a method of differentiating white blood cells using the white blood cell differentiation reagent.

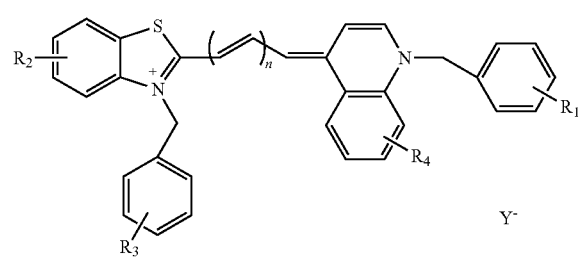

Formula I

27 Claims, 3 Drawing Sheets

U.S. PATENT DOCUMENTS

| | | |
|---|---|---|
| 5,389,549 A | 2/1995 | Hamaguchi et al. |
| 5,411,891 A | 5/1995 | Fan et al. |
| 5,413,938 A | 5/1995 | Tsujino et al. |
| 5,438,003 A | 8/1995 | Colella et al. |
| 5,486,477 A | 1/1996 | Carver et al. |
| 5,492,833 A | 2/1996 | Rodriguez et al. |
| 5,496,734 A | 3/1996 | Sakata et al. |
| 5,510,267 A | 4/1996 | Marshall |
| 5,516,695 A | 5/1996 | Kim et al. |
| 5,518,928 A | 5/1996 | Cremins et al. |
| 5,538,893 A | 7/1996 | Sakata et al. |
| 5,559,037 A | 9/1996 | Kim et al. |
| 5,616,501 A | 4/1997 | Rodriguez et al. |
| 5,618,733 A | 4/1997 | Sakata et al. |
| 5,633,167 A | 5/1997 | Fan et al. |
| 5,639,630 A | 6/1997 | Malin et al. |
| 5,639,666 A | 6/1997 | Shenkin et al. |
| 5,656,449 A | 8/1997 | Yue |
| 5,677,183 A | 10/1997 | Takarada et al. |
| 5,686,308 A | 11/1997 | Li et al. |
| 5,691,204 A | 11/1997 | Kim et al. |
| 5,731,206 A | 3/1998 | Ledis et al. |
| 5,733,784 A | 3/1998 | Studholme et al. |
| 5,747,343 A | 5/1998 | Tsuchiya et al. |
| 5,763,280 A | 6/1998 | Li et al. |
| 5,773,299 A | 6/1998 | Kim et al. |
| 5,786,224 A | 7/1998 | Li et al. |
| 5,817,518 A | 10/1998 | Li et al. |
| 5,821,127 A | 10/1998 | Akai et al. |
| 5,821,128 A | 10/1998 | Provost |
| 5,840,515 A | 11/1998 | Provost |
| 5,843,608 A | 12/1998 | Li et al. |
| 5,858,667 A | 1/1999 | Dertinger et al. |
| 5,874,311 A | 2/1999 | Li et al. |
| 5,879,900 A | 3/1999 | Kim et al. |
| 5,882,934 A | 3/1999 | Yi et al. |
| 5,891,731 A | 4/1999 | Akai et al. |
| 5,928,949 A | 7/1999 | Sakata et al. |
| 5,958,776 A | 9/1999 | Sakata et al. |
| 5,968,832 A | 10/1999 | Uchihashi et al. |
| 5,994,089 A | 11/1999 | Siiman et al. |
| 5,994,138 A | 11/1999 | Veriac |
| 6,060,322 A | 5/2000 | Horton et al. |
| 6,100,038 A | 8/2000 | Dertinger et al. |
| 6,114,130 A | 9/2000 | Veriac et al. |
| 6,114,173 A | 9/2000 | Zelmanovic et al. |
| 6,197,593 B1 | 3/2001 | Deka et al. |
| 6,245,499 B1 | 6/2001 | Suzuki et al. |
| 6,271,035 B1 | 8/2001 | Deka et al. |
| 6,287,791 B1 | 9/2001 | Terstappen et al. |
| 6,350,613 B1 | 2/2002 | Wardlaw et al. |
| 6,368,864 B1 | 4/2002 | Deka et al. |
| 6,495,692 B1 | 12/2002 | Wang et al. |
| 6,524,858 B1 | 2/2003 | Zelmanovic et al. |
| 6,551,831 B2 | 4/2003 | Gupta et al. |
| RE38,131 E | 6/2003 | Uchihashi et al. |
| 6,630,990 B2 | 10/2003 | van't Dever et al. |
| 6,632,676 B1 | 10/2003 | Crews et al. |
| 6,664,110 B1 | 12/2003 | Tsuji et al. |
| 6,794,152 B2 | 9/2004 | Ryan et al. |
| 6,869,798 B2 | 3/2005 | Crews et al. |
| 6,900,023 B1 | 5/2005 | Houwen et al. |
| 6,955,872 B2 | 10/2005 | Maples et al. |
| 6,977,156 B2 | 12/2005 | Ryan et al. |
| 7,083,982 B2 | 8/2006 | Wang et al. |
| 7,235,404 B2 | 6/2007 | Lang et al. |
| 7,300,797 B2 | 11/2007 | van Agthoven et al. |
| 7,405,082 B2 | 7/2008 | Mizukami et al. |
| 7,449,337 B2 | 11/2008 | Deka et al. |
| 7,465,584 B2 | 12/2008 | Matsumoto et al. |
| 2002/0182623 A1 | 12/2002 | Lefevre et al. |
| 2004/0241769 A1 | 12/2004 | Crews et al. |
| 2005/0202400 A1 | 9/2005 | Tsuji et al. |
| 2005/0272026 A1 | 12/2005 | Oguni |
| 2006/0177347 A1 | 8/2006 | Larsen et al. |
| 2007/0111276 A1 | 5/2007 | Lefevre et al. |
| 2007/0178597 A1 | 8/2007 | Tsuji et al. |
| 2008/0026475 A1 | 1/2008 | van Agthoven et al. |
| 2008/0131898 A1 | 6/2008 | Tsuji et al. |
| 2008/0176274 A1 | 7/2008 | Tsuji et al. |
| 2009/0017441 A1 | 1/2009 | Peng et al. |
| 2009/0176270 A1 | 7/2009 | Shao |
| 2010/0151509 A1 | 6/2010 | Ting et al. |
| 2010/0178654 A1 | 7/2010 | Kataoka et al. |

FOREIGN PATENT DOCUMENTS

| | | |
|---|---|---|
| CN | 1101982 | 4/1995 |
| CN | 1202621 | 12/1998 |
| EP | 0548983 | 6/1993 |
| EP | 0794435 | 9/1997 |
| WO | WO9717471 | 5/1997 |
| WO | WO03104771 | 12/2003 |

OTHER PUBLICATIONS

U.S. Appl. No. 12/482,335, filed Jun. 10, 2009, Shao Jianhui.
U.S. Appl. No. 12/580,474, filed Oct. 16, 2009, Yuji.
Stephen J. Mason et al., "Solid-Phase Catch, Activate, and Release Synthesis of Cyanine Dyes." American Chemical Society Organic Letters 2002, vol. 4 No. 24, pp. 4261-4264.
Notice of Allowance dated Aug. 7, 2009 for U.S. Appl. No. 11/967,991.
U.S. Appl. No. 12/843,671, filed Jul. 26, 2010, Zhao et al.

WHITE BLOOD CELL DIFFERENTIATION REAGENT CONTAINING AN ASYMMETRIC CYANINE FLUORESCENT DYE AND METHOD OF USE THEREOF

RELATED APPLICATIONS

The present application claims priority to Chinese Patent Application No. 200710139172.7, filed on Jul. 20, 2007, and entitled "White Blood Cell Differentiation Reagent and Method of Use Thereof," which is fully incorporated herein by reference.

TECHNICAL FIELD

The present disclosure relates to a white blood cell differentiation reagent and method of use thereof, and more particularly to a reagent and method for automatic differentiation of various subgroups of white blood cells in the blood using a suitable electronic apparatus such as a flow cytometry system or a fully automated hematology analyzer.

DETAILED DESCRIPTION

The white blood cells in normal peripheral blood are commonly classified into five types, i.e., lymphocyte, monocyte, neutrophil, eosinophil and basophil. Analysis of the white blood cell populations in a blood sample provides useful information for the clinical diagnosis of a multiplicity of diseases. For example, the onset of a disease may be associated with a change in the proportion and amount of different types of white blood cells in the blood, accompanied by the occurrence of abnormal white blood cells such as abnormal lymphocytes and immature granulocytes, etc. Therefore, differentiation and analysis of various types of normal and abnormal white blood cells may provide information regarding the latency, onset and development stages of a disease.

Traditional blood sample analysis mainly involves smearing the blood sample, staining the inner structures of the cells with a specific dye and determining the types and numbers of various subgroups of white blood cells by observing the sample under a microscope. Such methods are usually time-consuming and may yield different results depending on the recognition abilities of the individual operator. Accordingly, a method has been developed for automatic analysis of white blood cell subgroups by using flow cytometry to count the white blood cells.

At present, there are many methods for classifying white blood cells in a blood sample, including methods that make use of a combination of frequency, high-angle dispersion, low-angle dispersion, impedance, lateral dispersion, etc., or methods involving several steps. The current instrumental analysis mainly employs hemolytic agents to lyse the red blood cell systems and cause the white blood cells to generate different degrees of shrinkage that lead to differences in cell size and scattered light intensity.

U.S. Pat. No. 4,751,179 discloses a reagent system and an automatic cell counting apparatus that can determine four of the white blood cell subgroups, i.e., lymphocyte, monocyte, neutrophil and eosinophil. However, the system requires heating the sample mixture at 60-75° C., which increases the complexity and cost of the apparatus. Moreover, abnormal lymphocytes and immature granulocytes cannot typically be recognized.

China Patent Nos. CN1084473C and CN1113241C disclose four-part differential reagents for white blood cells and measuring reagents for basophils, as well as methods for using them to differentiate the white blood cells into five types. According to these patent documents, the methods as provided therein employ narrow-angle scattered light to detect information about cell size, and wide-angle scattered light to detect information about cell morphology, thereby achieving the four-part differentiation of the white blood cells. The basophils are singly detected by the basophilic reagent in light of these patent techniques, thereby achieving the five-part differentiation of white blood cells. The characteristics of the methods provided in the above-mentioned patents lie in using organic acid compounds to adjust the morphological information of the white blood cells. However, the preparation of these reagents is complex, and organic acids are needed to ensure recognition of acidophiles. In addition, these methods fail to detect abnormal white blood cells.

U.S. Pat. No. 6,004,816 discloses a method for labeling intracellular RNA using fluorescent dyes, comprising differentiating and counting the white blood cells through lateral scattered light and fluorescence intensity, and recognizing and counting abnormal lymphocytes and immature granulocytes. However, the fluorescent dyes as used are weak in light stability, and may easily cause experimental errors. Meanwhile, the low quantum excitation efficiency of these dyes requires a stronger intensity of the excitation light to ensure the effect of differentiation, thereby imposing a relatively high requirement on the apparatus. Moreover, these dyes mainly label intracellular RNA and show a weak binding ability to intracellular DNA, which hinders the accurate differentiation of some of the abnormal cells, such as abnormal lymphocytes and immature granulocytes that are rich in DNA. In addition, the sophisticated preparation of the dyes requires organic acids, amino acids, etc., and therefore is not cost-efficient.

Accordingly, there remains a need for a novel reagent and method for differentiating and counting normal white blood cells in the blood, while also recognizing abnormal white blood cells in the blood. It would be desirable if the method has good accuracy and precision and is inexpensive.

The following terms as used herein have the following meanings, unless otherwise specified.

The term "blood" or "blood sample" as used herein refers to a body fluid sample containing blood cells, e.g., peripheral blood, bone marrow fluid, etc.

The term "abnormal cells" as used herein refers to cells that are not commonly present in the blood, including immature cells and abnormal mature cells, for example, immature lymphocytes, immature marrow cells (also referred to herein as "Blast cells"), abnormal mature lymphocytes, abnormal mature marrow cells, nucleated red blood cells, etc.

The term "alkyl" as used herein refers to a straight or branched hydrocarbon group having 1-20 carbon atoms. Said alkyl group may optionally be substituted with one or more substituents, such as halogen, hydroxyl, cyano, nitro, amino, sulfhydryl, alkoxy, aryl, aralkyl, heterocyclyl, haloalkyl, haloaryl, haloaralkyl, etc. The substitution may desirably form chemically stable compounds and desirably does not influence the fluorescence properties of the fluorescent dye compounds disclosed.

The term "alkenyl" as used herein refers to a straight or branched hydrocarbon group having 2-20 carbon atoms and at least one carbon-carbon double bond. Said alkenyl group may optionally be substituted with one or more substituents, such as halogen, hydroxyl, cyano, nitro, amino, sulfhydryl, alkoxy, aryl, aralkyl, heterocyclyl, haloalkyl, haloaryl, haloaralkyl, etc. The substitution may desirably form chemically stable compounds and desirably does not influence the fluorescence properties of the fluorescent dye compounds disclosed.

The term "alkynyl" as used herein refers to a straight or branched hydrocarbon group having 2-20 carbon atoms and at least one carbon-carbon triple bond. Said alkynyl group may optionally be substituted with one or more substituents, such as halogen, hydroxyl, cyano, nitro, amino, sulfhydryl, alkoxy, aryl, aralkyl, heterocyclyl, haloalkyl, haloaryl, haloaralkyl, etc. The substitution may desirably form chemically stable compounds and desirably does not influence the fluorescence properties of the fluorescent dye compounds disclosed Fluorescent Dye The fluorescent dye compound of the present disclosure can specifically bind to intracellular nucleic acids (RNA, DNA). The fluorescent dye compound may be a red-light-excited fluorescent dye that can be excited by light emitted from an apparatus that provides laser light in the red spectral region, such as a red semiconductor laser, so that the reagent of the present invention can be used in blood analyzers or flow cytometers that utilize an inexpensive semiconductor laser as the light source.

The present disclosure provides a reagent that can help differentiate and count normal white blood cells in the blood, and at the same time can recognize abnormal white blood cells (such as abnormal lymphocytes and immature granulocytes) in the blood. This reagent includes a fluorescent dye compound having the following structure:

Formula I wherein $R_1, R_2, R_3$ and $R_4$ are independently selected from H, $C_{1-20}$alkyl, $C_{2-20}$alkenyl and $C_{2-20}$alkynyl; n is 1, 2 or 3; and $Y^-$ is an anion.

In one embodiment, the fluorescent dye compound has the molecular structure of Formula II:

Formula II

In one embodiment, the reagent further includes a red blood cell lysing agent, which may include one or more of the following: a cationic surfactant, a nonionic surfactant, a buffer or any combination thereof, and may optionally comprise alcohols.

In another aspect, the present disclosure provides a white blood cell detection kit that comprises the white blood cell differentiation reagent as described herein.

In a further aspect, the present disclosure provides a method for differentiating white blood cells in a blood sample, including the following steps: (1) mixing the blood sample with a suitable amount of solution of a red blood cell lysing agent, (2) adding a solution of a fluorescent dye compound of Formula I into the mixture of step 1, Formula I wherein $R_1, R_2, R_3$ and $R_4$ are independently selected from H, $C_{1-20}$alkyl, $C_{2-20}$alkenyl and $C_{2-20}$alkynyl; n is 1, 2 or 3; and $Y^-$ is an anion; (3) measuring at least one kind of scattered light parameters and at least one kind of fluorescence parameters of the resulting mixture of step 2; and (4) differentiating and/or counting the white blood cells according to the at least one kind of scattered light parameters and fluorescence parameters Alternatively, the present disclosure provides an alternative method for differentiation of white blood cells in a blood sample, wherein the solution of the red blood cell lysing agent and the solution of the fluorescent dye are added to the blood sample simultaneously.

The fluorescent dye compounds of the present disclosure can be dissolved in ethanol, DMSO or ethylene glycol and preserved therein in the form of a stock solution, or can be dissolved in other nonaqueous solvents. In one embodiment, ethylene glycol may be used as the solvent, which optionally contains 5-10 percent methanol as a component of the dilution solution. To prevent the fluorescent dye from aggregating, the present disclosure may also optionally comprise nonionic surfactants as the dispersant so that the fluorescent dye compound maintains a certain solubility and does not tend to aggregate. Such nonionic surfactants include, for example, polyoxyethylene glycol (POE), polyoxypropylene glycol (POP), polyoxyethylene glycol-polyoxypropylene glycol (POE-POP) and Brij series nonionic surfactants. In one embodiment, Brij 35, Brij 56 or the like may be used as the dispersant for the fluorescent dye compound, with the concentration being between 0.02-2.0 percent.

Alternatively, the fluorescent dye compounds of the present disclosure can be formulated with the red blood cell lysing agent to form a single-component reagent.

Red Blood Cell Lysing Agent

The red blood cell lysing agent as used herein may include one of: a cationic surfactant, a nonionic surfactant, a buffer or any combination thereof.

The present disclosure utilizes a combination of the cationic surfactant and the nonionic surfactant as a reagent for lysing the red blood cells in a blood sample. In addition to lysing the red blood cells, the combination can also suitably break up the membrane structure of various subgroups of white blood cells so that each white blood cell subgroup in the blood shrinks into an appropriate size. In this way, different degrees of aggregations occur to the intracellular structures, causing differences in the scattered light properties. Exemplary cationic surfactants can be octyltrimethyl ammonium bromide (OTAB), decyltrimethyl ammonium bromide

(DTAB), lauryltrimethyl ammonium chloride (LTAC), cetyl trimethyl ammonium bromide (CTAB) or cetyl trimethyl ammonium chloride (CTAC). In one exemplary embodiment, LTAC may be used at a concentration of between 300-800 mg/L. In one embodiment, the nonionic surfactants can be polyoxyethylene nonionic surfactants, for example, long chain fatty alcohol polyoxyethylene ether, alkylphenol polyoxyethylene ether, fatty acid polyoxyethylene ester, fatty amine polyoxyethylene ether, etc. One exemplary nonionic surfactant is polyoxyethylene (23) lauryl ether (Brij 35), with a concentration of between 1-5 g/L.

The reagent of the present disclosure may contain a buffer that maintains the pH and serves to suitably dilute the blood sample. The buffer can maintain the pH in a constant range to stabilize the staining effect of various subgroups of white blood cells. The concentration of the buffer may be in the range of between 0.01-200 mM. There is no particular limitation to the type of buffer. The buffer can be, for example, carboxylate salts, phosphate salts, citrate salts, Tris-HCl or MOPS, as well as other organic buffers at a suitable concentration. The suitable pH of the reagent varies depending on the particular fluorescent dye compound selected and is generally in the range of between pH 7.0-8.0, such as at pH 7.0. A Tris-HCl or MOPS buffering system may be used in one embodiment.

The red blood cell lysing agent may also optionally include a suitable proportion of alcohols, e.g., methanol, to facilitate the aggregation of the inner structures of white blood cells.

Detection Kit

In another aspect, the present disclosure provides a white blood cell detection kit useful for differentiation and counting of normal white blood cells in the blood, and at the same time useful for recognition of abnormal white blood cells (such as abnormal lymphocytes and immature granulocytes) in the blood. The detection kit may include a white blood cell differentiation reagent that comprises the fluorescent dye compound of Formula I, having the following structure:

I wherein $R_1$, $R_2$, $R_3$ and $R_4$ are independently selected from H, $C_{1-20}$alkyl, $C_{2-20}$alkenyl and $C_{2-20}$alkynyl; n is 1, 2 or 3; and $Y^-$ is an anion.

In one embodiment, the fluorescent dye compound has the following structure of Formula II:

Formula II

The white blood cell differentiation reagent may further include the red blood cell lysing agent described above.

In one embodiment, the fluorescent dye compound exists in the form of a stock solution and is preserved in a separate container.

In another embodiment, the fluorescent dye compound is formulated with the red blood cell lysing agent as a single-component solution.

The detection kit may include a separate fluorescent dye stock that is suitably sealed in at least one container. The detection kit can also include other white blood cell differentiation reagents for the differentiation of white blood cells in the blood and instructions on how to identify the white blood cells. The detection kit can further include a control sample or a series of control samples that can be detected and compared with the test samples. Each individual component of the detection kit can be sealed in a single container, and these containers, together with the instructions, can all be packed in a single package. Such detection kits may be useful for the differentiation and/or counting of various white blood cells in the blood.

Method of Use

In another aspect, the present disclosure further provides a method for the differentiation and/or counting of white blood cells in the blood. In brief, a blood sample is mixed with the reagent disclosed herein, and measurement is then made on at least one kind of scattered light parameters and at least one kind of fluorescence parameters of the sample. Thereafter, the sample is differentiated and/or counted based on the scattered light parameters and the fluorescence parameters.

The blood sample used can either be whole blood or component blood. The blood sample can first be mixed with the red blood cell lysing agent and the buffer so that the red blood cells are lysed and the various subgroups of white blood cells shrink to different degrees. At the same time, small pores are formed on the cell membranes of the detected white blood cells, sufficient to allow the molecules of the fluorescent dye to pass through the cell membranes.

Subsequently or simultaneously with mixing the red blood cell lysing agent, the stock solution of the fluorescent dye is added to fluorescently label the white blood cells. When the blood sample is mixed with the reagent disclosed herein, the total volume of the blood sample and the reagent may ensure that a sufficient concentration of cells will pass through the detection channel of the apparatus. The reagent composition may dilute the blood sample to a proportion of 10:1, 50:1 or 100:1, or any value in any of the above ranges, so long as the dilution meets the requirements of practical use. Such adjustment is within the capability of those skilled in the art with the aid of the present disclosure.

The sample mixture can be incubated in an incubation chamber for a period of less than 40 seconds, such as 24 seconds, at any suitable temperature, e.g., 42° C. Then the diluted and stained blood sample is introduced into the flow chamber and passed through the detection channel of the blood analyzer or similar flow cytometer, where at least one scattered light parameter and at least one fluorescence parameter of the white blood cells are detected and analyzed.

The term "scattered light" as referred to in the present disclosure means scattered light that can be detected by commercially-available blood analyzers or similar flow cytometers. Such scattered light includes, but is not limited to, a lateral scattered light, a forward low-angle scattered light (light-receiving angle of about 0-5°) and a forward high-angle scattered light (light-receiving angle of about 5-20°). Scattered light with such an angle reflects information about the size and internal structures of the white blood cells, and is therefore used as the scattered light for the present disclosure. In one embodiment, lateral scattered light is used.

The fluorescent dye compound that binds to intracellular nucleic acids such as DNA and RNA emits fluorescence. The fluorescence property is a parameter that reflects the amount of fluorescent dye inside the cells in the blood sample. Because differences in the metabolic activities of various subgroups of cells lead to differences in the nucleic acid content, the fluorescence properties of the various subgroups of white blood cells differ in some aspects. Depending on the particular dye used, an excitation light of a suitable wavelength is selected, and the emitted light of the corresponding wavelength is monitored. Laser light in the red spectral region emitted by a red semiconductor laser may be used as the light source for detection. There is no special limitation on the light source for the red spectral region, so long as it can emit red light near the excitation wavelength of the selected fluorescent dye, e.g., light of a wavelength of between about 600-680 nm. The light source may be, for example, a He—Ne laser or a semiconductor laser in the red spectral region. The semiconductor laser may be used because it is less expensive and smaller in dimension than other lasers, so that the cost and dimension of the apparatus can be reduced.

The scattered light parameters and the fluorescence parameters may be utilized to recognize various subgroups of white blood cells and acquire information about possible abnormal lymphocytes and immature granulocytes, to classify and count the scattering dots of various clusterings, and to calculate the percentages of various subgroups of white blood cells. The scattered light reflects the degree of granularity inside the cells. The degree of granularity of different subgroups of white blood cells is roughly as follows: the eosinophils have two foliate nuclei and many cytoplasmic granules that can be stained by acidic fluorescent dyes; the neutrophils have foliate or bacillar nuclei and more intracellular granules; the monocytes have a single big nucleus and less intracellular granules; and the lymphocytes have a single big nucleus and essentially no granules. Therefore, the order of intensity of the scattered light from various subgroups of white blood cells under the same conditions is EO (eosinophil)>NEUT (neutrophil)>MONO (monocyte)>LYM (lymphocyte).

The following specific examples are included for illustrative purposes only and are not to be considered as limiting to this disclosure. The reagents and intermediates used in the following examples are either commercially available or can be prepared according to standard literature procedures by those skilled in the art of organic synthesis.

EXAMPLES

Example 1

Synthesis of Dye

An illustrative fluorescent dye compound is synthesized in the following manner, wherein said dye compound has the following structure of Formula II:

Formula II 20 mmol of 2-methylbenzothiazole and 22 mmol of benzyl bromide are added under argon protection into a 50-ml round bottom flask containing 20 ml of benzene, and the reaction mixture is heated to reflux for 24 hours. After the mixture cools down, the precipitate is filtered and the filter cake is washed with ethyl ether and dried to afford a pale pink solid powder in a crude yield of 58 percent, which is the intermediate 1-benzyl-2-methylbenzothiazole quaternary ammonium salt.

10 mmol of 1-benzyl-2-methylbenzothiazole quaternary ammonium salt and 30 mmol of N,N'-diphenylformamidine are added in 60 ml of acetic acid, and heated under stirring in a 90° C. oil bath for 1.5 hours. The resulting red oily mass is washed with petroleum ether in suspension three times to remove the acetic acid. Then a certain amount of ethyl ether is added to precipitate an orange solid powder, which is filtered and dried. This crude product is separated on a silica column using dichloromethane:methanol in the ratio of 100:3 as the eluent. The yellow fraction is collected, with a yield of 42 percent. Into the yellow fraction are added 4 mmol of 1-benzyl-4-methylquinoline quaternary ammonium salt and 10 ml of pyridine, and the mixture is heated under stirring in a 90° C. oil bath for 1.5 hours. The reaction liquor is poured into ethyl ether to precipitate dark purple little dye particles, which are filtered and dried. The dye is separated on a silica column using dichloromethane:methanol in the ratio of 100:5 as the eluent, and the blue fraction is collected in a yield of 70 percent.

$^1$H-NMR δ (400 MHz, CD3OD, TMS) 5.49 (s, 2H), 5.71 (s, 2H), 6.44 (d, 1H), 6.98 (d, 1H), 7.18-7.80 (m, 18H), 8.23 (t, 1H), 8.31 (d, 1H), 8.36 (d, 1H). MS (EI) $C_{33}H_{27}BrN_2S$ m/z: 483.2 $[M-Br]^+$.

Example 2

Formulation of Reagents

Reagent systems with the following composition are formulated:

A: stock solution of fluorescent dye:

| | |
|---|---|
| fluorescent dye | 30 mg |
| ethylene glycol | 900 ml |
| methanol | 100 ml |

B: solution of red blood cell lysing agents:

| | |
|---|---|
| LTAC | 550 mg |
| Brij 35 | 1.5 g |
| tris(hydroxymethyl)aminomethane (Tris) | 13 g |
| HCl (13N) | 5.8 ml |
| refined water | 1 L |

The solution is finally adjusted to pH 7.

Example 3

Analysis of Different Blood Samples and the Results

Figure 1:
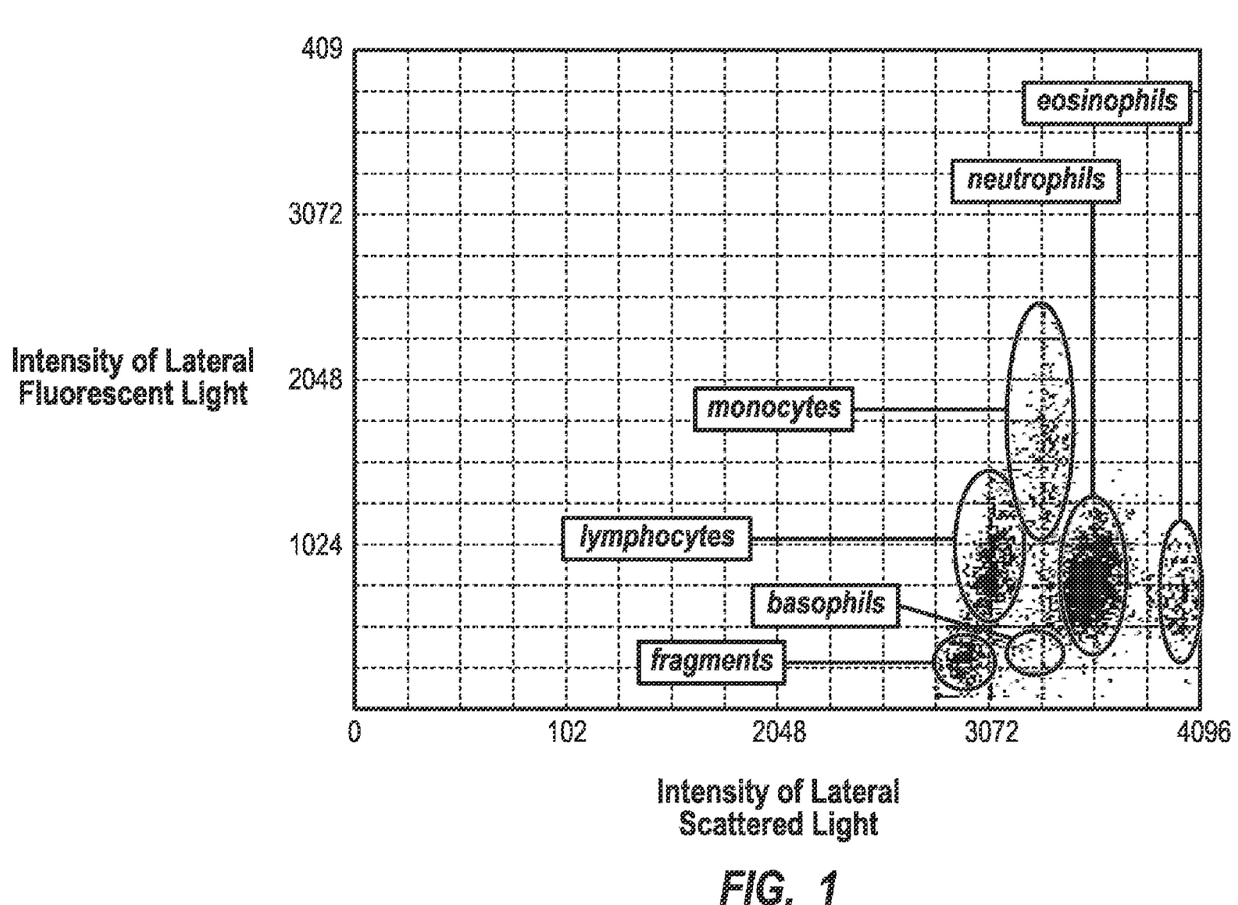
FIG. 1 is a two-dimensional sketch map showing an analysis of a normal blood sample (No. 1 blood sample) using the composition of Example 1.
Figure 2:
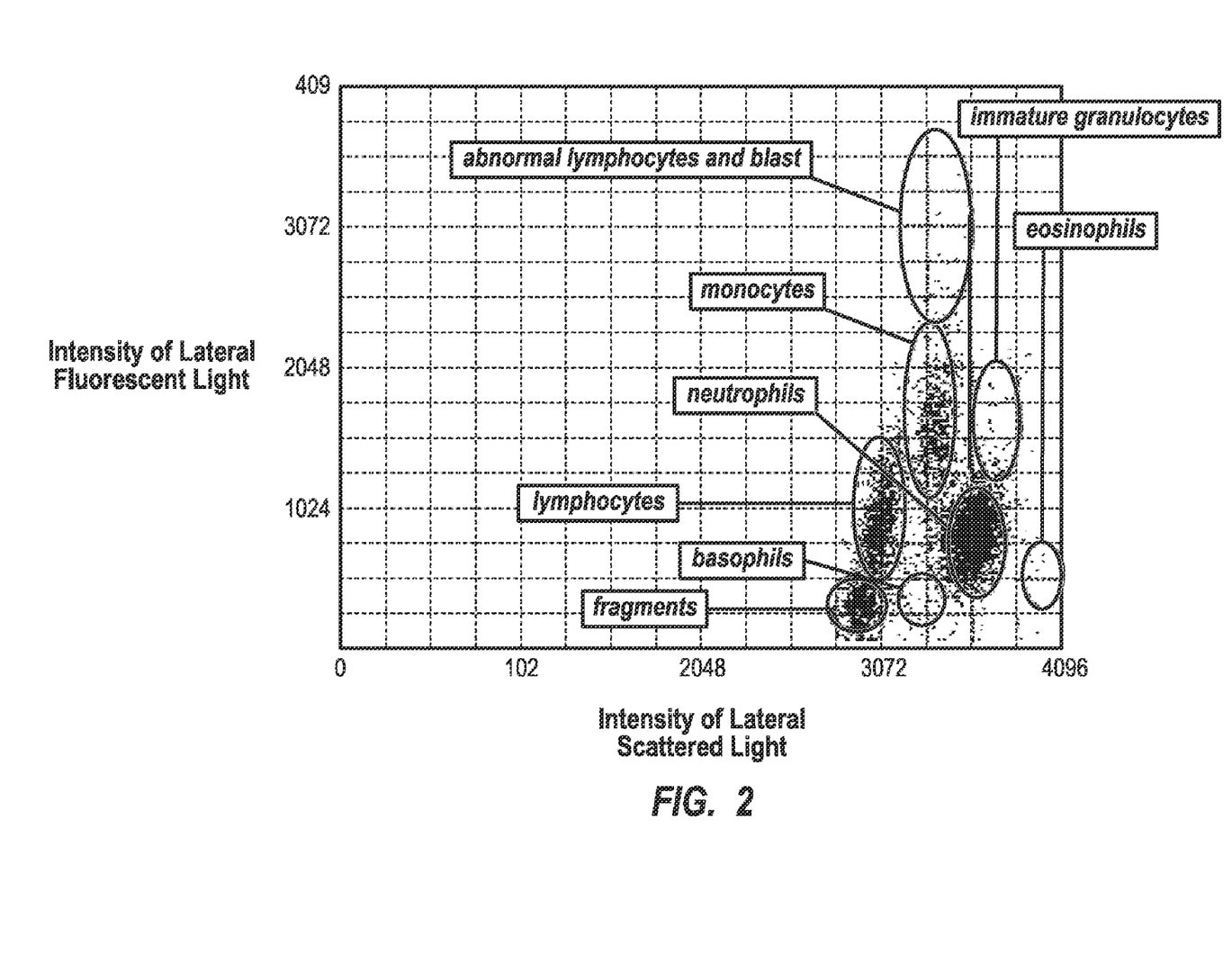
FIG. 2 is a two-dimensional sketch map showing an analysis of an abnormal blood sample (No. 2 blood sample) using the composition of Example 1.
Figure 3:
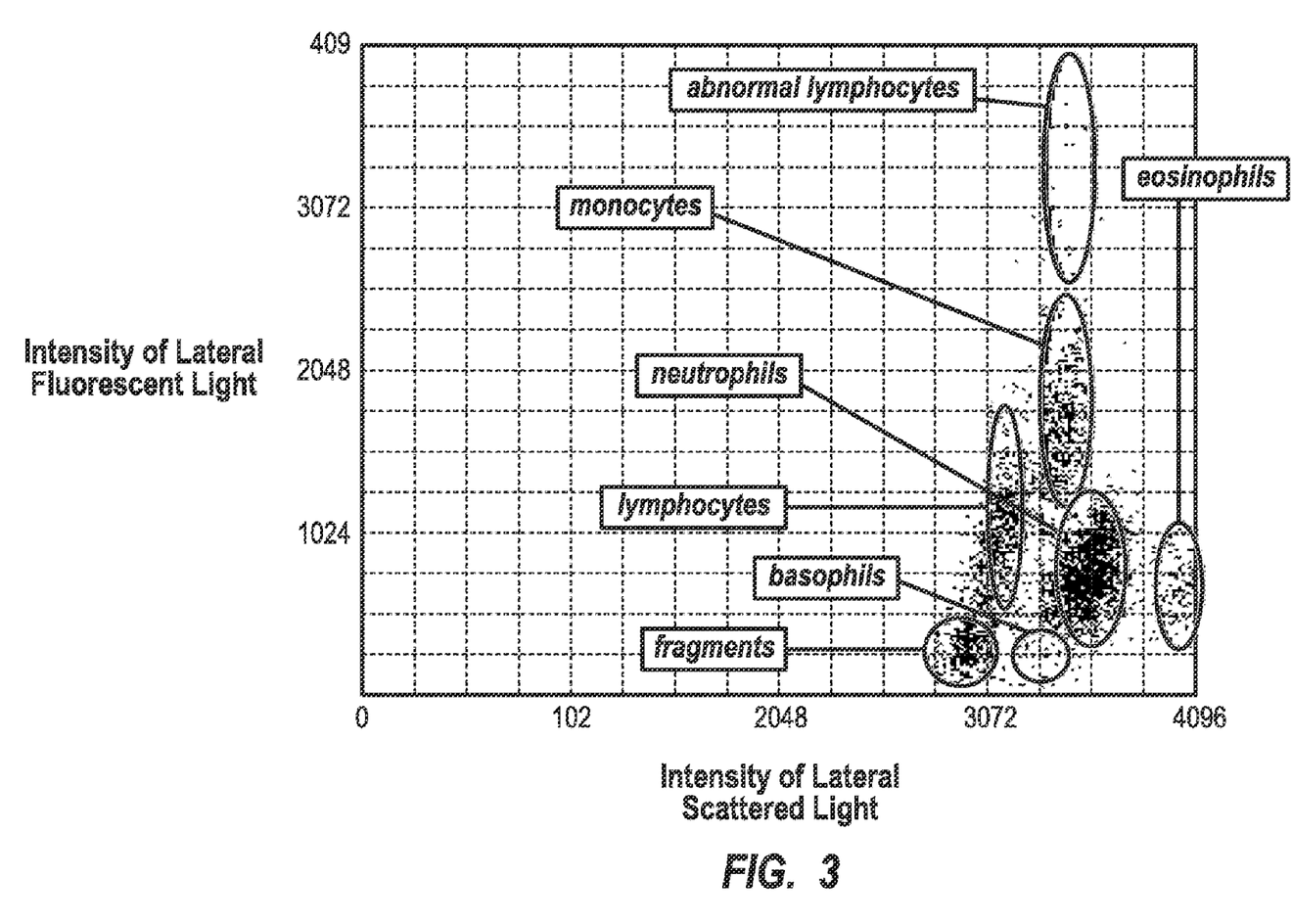
FIG. 3 is a two-dimensional sketch map showing an analysis of an abnormal blood sample (No. 3 blood sample) using the composition of Example 1.

1 ml of the red blood cell lysing agent is homogenized with 20 μl of blood treated with anticoagulant, and then 20 μl of stock solution of the fluorescent dye is added immediately therein. The mixture is homogenized and incubated in the incubation chamber at 42° C. for 24 seconds to form the test sample. The test sample is measured for the intensity of lateral scattered light and the intensity of lateral fluorescence. The detection result regarding the normal blood sample (No. 1 sample) as shown in FIG. 1 suggests that the compounds, compositions and methods disclosed herein can achieve the recognition and differentiation of five subgroups of white blood cells. The detection result regarding the abnormal blood sample (No. 2 sample) as shown in FIG. 2 suggests that the compounds, compositions and methods disclosed herein can effectively differentiate the eosinophils and can also effectively recognize abnormal white blood cells, including immature granulocytes and abnormal lymphocytes. The detection result regarding the abnormal blood sample (No. 3 sample) as shown in FIG. 3 suggests that the compounds, compositions and methods disclosed herein not only can effectively differentiate various subgroups of white blood cells, but also can effectively recognize abnormal lymphoid cells.

All data, figures, apparatuses, reagents and steps exemplified herein shall be interpreted as illustrative but not restrictive. Although the present disclosure has been described with reference to the above particular embodiments, many modifications and other variations will be obvious to those skilled in the art. All such modifications and other variations are within the spirit and scope of the present invention, as defined by the following claims.

What is claimed is:

1. A white blood cell differentiation reagent, comprising a fluorescent dye compound having the following Formula I:

Formula I wherein $R_1$, $R_2$, $R_3$ and $R_4$ are independently selected from the following: H, $C_{1-20}$alkyl, $C_{2-20}$alkenyl and $C_{2-20}$alkynyl, n is 1, 2 or 3, and $Y^-$ is an anion.

2. The white blood cell differentiation reagent according to claim 1, wherein the fluorescent dye compound has the following Formula II:

Formula II

3. The white blood cell differentiation reagent according to claim 1, wherein the fluorescent dye compound is present in a concentration of between 1 mg/L to 1,000 mg/L.

4. The white blood cell differentiation reagent according to claim 3, wherein the fluorescent dye compound has the following Formula II:

Formula II

5. The white blood cell differentiation reagent according to claim 1, wherein the fluorescent dye compound is present in a concentration of between 2 mg/L to 100 mg/L.

6. The white blood cell differentiation reagent according to claim 1, wherein the fluorescent dye compound is present in a concentration of between 5 mg/L to 50 mg/L.

7. The white blood cell differentiation reagent according to claim 1, wherein the fluorescent dye compound is present in a concentration of between 10 mg/L to 20 mg/L.

8. The white blood cell differentiation reagent according to claim 1, wherein the reagent further comprises a red blood cell lysing agent.

9. The white blood cell differentiation reagent according to claim 8, wherein the red blood cell lysing agent comprises at least one of the following: a cationic surfactant, a nonionic surfactant, a buffer or any combination thereof.

10. The white blood differentiation reagent according to claim 9, wherein the red blood cell lysing agent comprises a cationic surfactant selected from: octyltrimethyl ammonium bromide (OTAB), decyltrimethyl ammonium bromide (DTAB), lauryltrimethyl ammonium chloride (LTAC), cetyl trimethyl ammonium bromide (CTAB), or cetyl trimethyl ammonium chloride (CTAC) or mixtures thereof.

11. The white blood differentiation reagent according to claim 10, wherein the cationic surfactant comprises LTAC at a concentration of between 300 and 800 mg/L.

12. The white blood differentiation reagent according to claim 9, wherein the red blood cell lysing agent comprises a nonionic surfactant selected from: long chain fatty alcohol polyoxyethylene ether, alkylphenol polyoxyethylene ether, fatty acid polyoxyethylene ester, fatty amine polyoxyethylene ether or mixtures thereof.

13. The white blood differentiation reagent according to claim 12, wherein the nonionic surfactant comprises polyoxyethylene (23) lauryl ether (Brij 35) at a concentration of between 1 and 5 g/L.

14. The white blood differentiation reagent according to claim 9, wherein the red blood cell lysing agent comprises a buffer selected from: carboxylate salts, phosphate salts, citrate salts, Tris-HCl, MOPS or mixtures thereof.

15. The white blood differentiation reagent according to claim 14, wherein the buffer is selected from: Tris-HCl or MOPS.

16. The white blood differentiation reagent according to claim 14, wherein the buffer is configured to maintain a pH of a detection system at between 7.0 and 8.0.

17. The white blood differentiation reagent according to claim 9, wherein the red blood cell lysing agent further comprises an alcohol.

18. The white blood cell differentiation reagent according to claim 9, wherein the fluorescent dye compound is present in the form of a single stock solution.

19. The white blood cell differentiation reagent according to claim 1, wherein the fluorescent dye compound is present in the form of a single stock solution.

20. A white blood cell detection kit comprising the white blood cell differentiation reagent according to claim 1.

21. The detection kit according to claim 20, wherein the white blood cell differentiation reagent comprises a fluorescent dye compound having the following Formula II:

Formula II

22. The detection kit according to claim 20, wherein the fluorescent dye compound of the white blood cell differentiation reagent is present in the form of a single stock solution.

23. A method for differentiation of white blood cells in a blood sample, comprising:
   (i) mixing the blood sample with a solution of a red blood cell lysing agent;
   (ii) adding a solution of a fluorescent dye compound of Formula I to the blood sample:

Formula I wherein $R_1$, $R_2$, $R_3$, $R_4$, $Y^-$ and n are as defined in claim 1;
   (iii) measuring at least one kind of scattered light parameters and at least one kind of fluorescence parameters of the resulting mixture of step ii; and
   (iv) differentiating and/or counting the white blood cells according to the at least one kind of scattered light parameters and fluorescence parameters.

24. The method according to claim 23, wherein the fluorescent dye compound has the following Formula II:

Formula II

25. The method according to claim 23, wherein adding the solution of fluorescent dye compound comprises adding the solution of the red blood cell lysing agent and the solution of the fluorescent dye compound to the sample simultaneously.

26. The method according to claim 25, wherein the fluorescent dye compound has the following Formula II:

Formula II

27. The method according to claim 23, wherein adding the solution of fluorescent dye compound comprises adding the fluorescent dye compound to the blood sample subsequent to mixing the blood sample with the solution of the red blood cell lysing agent.

* * * * *